United States Patent
Green et al.

(10) Patent No.: US 11,434,540 B2
(45) Date of Patent: Sep. 6, 2022

(54) ULTRASPECIFIC NUCLEIC ACID SENSORS FOR LOW-COST LIQUID BIOPSIES

(71) Applicant: Arizona Board of Regents on Behalf of Arizona State University, Scottsdale, AZ (US)

(72) Inventors: Alexander Green, Scottsdale, AZ (US); Fan Hong, Mesa, AZ (US); Soma Chaudhary, Tempe, AZ (US); Anli Tang, Gilbert, AZ (US); Hao Yan, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 455 days.

(21) Appl. No.: 16/349,752

(22) PCT Filed: Nov. 15, 2017

(86) PCT No.: PCT/US2017/061796
§ 371 (c)(1),
(2) Date: May 14, 2019

(87) PCT Pub. No.: WO2018/093898
PCT Pub. Date: May 24, 2018

(65) Prior Publication Data
US 2020/0071777 A1    Mar. 5, 2020

Related U.S. Application Data

(60) Provisional application No. 62/422,331, filed on Nov. 15, 2016.

(51) Int. Cl.
*C12Q 1/6858* (2018.01)
*C12Q 1/6897* (2018.01)

(52) U.S. Cl.
CPC ......... *C12Q 1/6897* (2013.01); *C12Q 1/6858* (2013.01); *C12Q 2525/301* (2013.01); *C12Q 2527/101* (2013.01); *C12Q 2531/101* (2013.01); *C12Q 2537/1373* (2013.01)

(58) Field of Classification Search
CPC ............... C12Q 1/6896; C12Q 1/6858; C12Q 2525/301; C12Q 2527/101; C12Q 2531/101; C12Q 2537/1373
See application file for complete search history.

(56) References Cited

U.S. PATENT DOCUMENTS

| | | | |
|---|---|---|---|
| 10,550,440 B2 | 2/2020 | Green | |
| 2013/0274135 A1 | 10/2013 | Zhang et al. | |
| 2015/0361475 A1* | 12/2015 | Marras | C12Q 1/686 435/91.2 |
| 2016/0076083 A1 | 3/2016 | Ellington et al. | |
| 2016/0153036 A1 | 6/2016 | Chen et al. | |
| 2019/0071737 A1 | 3/2019 | Green | |
| 2019/0185856 A1 | 6/2019 | Green | |
| 2019/0218624 A1 | 7/2019 | Green | |
| 2019/0256898 A1 | 8/2019 | Green | |
| 2019/0276901 A1 | 9/2019 | Green | |
| 2019/0285620 A1 | 9/2019 | Green | |
| 2019/0382746 A1 | 12/2019 | Green | |

FOREIGN PATENT DOCUMENTS

| | | |
|---|---|---|
| WO | 2015/058008 | 4/2015 |
| WO | 2015/184016 | 12/2015 |
| WO | 2016/011089 | 1/2016 |
| WO | 2017147585 A1 | 8/2017 |
| WO | 2017205668 A1 | 11/2017 |
| WO | 2018026762 A1 | 2/2018 |
| WO | 2018026765 A1 | 2/2018 |
| WO | 2018027177 A1 | 2/2018 |
| WO | 2018075502 A1 | 4/2018 |
| WO | 2018112350 A1 | 6/2018 |
| WO | 2018187687 A1 | 10/2018 |

OTHER PUBLICATIONS

Barbano, R., et al. "Competitive allele-specific TaqMan PCR (Cast-PCR) is a sensitive, specific and fast method for BRAF V600 mutation detection in melanoma patients." Scientific reports 5 (2015): 18592.
Bettegowda, C., et al. "Detection of circulating tumor DNA in early- and late-stage human malignancies." Science translational medicine 6.224 (2014): 224ra24-224ra24.
Bidard, F.-C., et al. "Going with the flow: from circulating tumor cells to DNA." Science translational medicine 5.207 (2013): 207ps14-207ps14.
Clancy, E., et al. "Development of a rapid recombinase polymerase amplification assay for the detection of *Streptococcus pneumoniae* in whole blood." BMC infectious diseases 15.1 (2015): 481.
Crannell, Z. A., et al. "Equipment-free incubation of recombinase polymerase amplification reactions using body heat." PloS one 9.11 (2014): e112146.
Diehl, F., et al. "BEAMing: single-molecule PCR on microparticles in water-in-oil emulsions." Nature methods 3.7 (2006): 551.

(Continued)

*Primary Examiner* — David C Thomas
(74) *Attorney, Agent, or Firm* — Quarles & Brady, LLP

(57) ABSTRACT

Ultraspecific, programmable nucleic acid sensors capable of detecting and preferentially amplifying target DNA molecules comprising a particular SNP or mutation are provided. In some cases, the ultraspecific programmable nucleic acid sensors are useful for detecting SNP-containing DNA molecules indicative of cancer such as cell-free DNA circulating in the blood or indicative of organ transplant rejection Also provided are methods for construction of such ultraspecific nucleic acid sensors and methods for preferential amplification of target DNA molecules containing a mutation of interest, as well as testing systems for early cancer screening and routine monitoring of circulating cancer DNA using liquid biological samples such as serum, plasma, or saliva.

4 Claims, 12 Drawing Sheets

(56) References Cited

OTHER PUBLICATIONS

Diehl, F., et al. "Detection and quantification of mutations in the plasma of patients with colorectal tumors." Proceedings of the National Academy of Sciences 102.45 (2005): 16368-16373.
Forshew, T., et al. "Noninvasive identification and monitoring of cancer mutations by targeted deep sequencing of plasma DNA." Science translational medicine 4.136 (2012): 136ra68-136ra68.
Garcia-Murillas, I., et al. "Mutation tracking in circulating tumor DNA predicts relapse in early breast cancer." Science translational medicine 7.302 (2015): 302ra133-302ra133.
Gormally, E., et al. "Circulating free DNA in plasma or serum as biomarker of carcinogenesis: practical aspects and biological significance." Mutation Research/Reviews in Mutation Research 635. 2-3 (2007): 105-117.
Green, A. A., et al. "Toehold switches: de-novo-designed regulators of gene expression." Cell 159.4 (2014): 925-939.
Kersting, S., et al. "Rapid detection of Plasmodium falciparum with isothermal recombinase polymerase amplification and lateral flow analysis." Malaria journal 13.1 (2014): 99.
Li, J., et al. "Advances in isothermal amplification: novel strategies inspired by biological processes." Biosensors and Bioelectronics 64 (2015): 196-211.
Li, J., et al. "Replacing PCR with COLD-PCR enriches variant DNA sequences and redefines the sensitivity of genetic testing." Nature medicine 14.5 (2008): 579.
Menard, D., et al. "A worldwide map of Plasmodium falciparum K13-propeller polymorphisms." New England Journal of Medicine 374.25 (2016): 2453-2464.
Milbury, C. A., et al. "Ice-COLD-PCR enables rapid amplification and robust enrichment for low-abundance unknown DNA mutations." Nucleic acids research 39.1 (2010): e2-e2.
Morlan, J. et al. "Mutation detection by real-time PCR: a simple, robust and highly selective method." PloS one 4.2 (2009): e4584.
Motiwala, A. S., et al. "Mutations in extensively drug-resistant *Mycobacterium tuberculosis* that do not code for known drug-resistance mechanisms." The Journal of infectious diseases 201.6 (2010): 881-888.
Murtaza, M., et al. "Non-invasive analysis of acquired resistance to cancer therapy by sequencing of plasma DNA." Nature 497.7447 (2013): 108.
Pardee, K., et al. "based synthetic gene networks." Cell 159.4 (2014): 940-954.

Pardee, K., et al. "Rapid, low-cost detection of Zika virus using programmable biomolecular components." Cell 165.5 (2016): 1255-1266.
Piepenburg, O., et al. "DNA detection using recombination proteins." PLoS biology 4.7 (2006): e204.
Pollack, A., "'Liquid' Cancer Test Offers Hope for Alternative to Painful Biopsies," New York Times (Jun. 4, 2016).
Rohrman, B. et al. "Inhibition of recombinase polymerase amplification by background DNA: a lateral flow-based method for enriching target DNA." Analytical chemistry 87.3 (2015): 1963-1967.
Schwarzenbach, H. et al. "Cell-free nucleic acids as biomarkers in cancer patients." Nature Reviews Cancer 11.6 (2011): 426.
Siravegna, G., et al. "Clonal evolution and resistance to EGFR blockade in the blood of colorectal cancer patients." Nature medicine 21.7 (2015): 795.
Straimer, J., et al. "K13-propeller mutations confer artemisinin resistance in Plasmodium falciparum clinical solates." Science 347.6220 (2015): 428-431.
Taly, V., et al. "Multiplex picodroplet digital PCR to detect KRAS mutations in circulating DNA from the plasma of colorectal cancer patients." Clinical chemistry 59.12 (2013): 1722-1731.
Thress, K. S., et al. "Acquired Egfr C797S mutation mediates resistance to AZD9291 in non-small cell lung cancer harboring EGFR T790M." Nature medicine 21.6 (2015): 560.
U.S. Appl. No. 16/322,719, Green et al., filed Feb. 1, 2019.
U.S. Appl. No. 16/468,846, Green, filed Jun. 12, 2019.
U.S. Appl. No. 16/603,338, Green et al., filed Oct. 7, 2019.
Vogelstein, B., et al. "Cancer genome landscapes." science 339. 6127 (2013): 1546-1558.
Wang, H., et al. "Allele-specific, non-extendable primer blocker PCR (AS-NEPB-PCR) for DNA mutation detection in cancer." The Journal of Molecular Diagnostics 15.1 (2013): 62-69.
Win, A. A., et al. "K13 mutations and pfmdr1 copy number variation in Plasmodium falciparum malaria in Myanmar." Malaria journal 15.1 (2016): 110.
Zhang, D. Y., et al. "Optimizing the specificity of nucleic acid hybridization." Nature chemistry 4.3 (2012): 208.
The International Search Report and Written Opinion for International Patent Application No. PCT/US2017/061796 dated Feb. 6, 2018.
Byrom et al. "Exquisite allele discrimination by toehold hairpin primers," Nucleic Acids Research, Sep. 2, 2014 (Sep. 2, 2014), vol. 42, No. 15: e120, pp. 1-13, entire document.

* cited by examiner

ULTRASPECIFIC NUCLEIC ACID SENSORS FOR LOW-COST LIQUID BIOPSIES

CROSS-REFERENCE TO RELATED APPLICATIONS

This application represents the national stage entry of PCT International Application No. PCT/US2017/061796, filed on Nov. 15, 2017, and, claims priority to U.S. Provisional Application No. 62/422,331, filed Nov. 15, 2016, each of which is incorporated by reference herein as if set forth in its entirety.

STATEMENT REGARDING FEDERALLY SPONSORED RESEARCH

The invention was made with government support under GM126892 awarded by the National Institutes of Health. The government has certain rights in the invention.

BACKGROUND

The detection of mutations in circulating cell-free DNA (cfDNA) in plasma or other bodily fluids has emerged as a potentially transformative and minimally invasive method for detecting and managing cancer. Biopsies for cancer diagnosis are invasive, costly, and require tissues to be removed from the body. Furthermore, biopsies provide only a local and time-limited view of the tumor and tumors can be inaccessible in many cases. Alternatively, protein-based biomarkers can be obtained from serum; however, clinically proven circulating protein biomarkers exist for only a minority of cancers. Accordingly, there remains a need in the art for highly specific nucleic acid tests that work in isothermal conditions and reliably identify oncogenes.

SUMMARY OF THE DISCLOSURE

In a first aspect, provided herein is a method for detecting a single nucleotide polymorphism (SNP)-containing DNA molecule in a sample. The method can comprise or consist essentially of (a) contacting an ultraspecific riboregulator to a sample, wherein the riboregulator is a synthetic nucleic acid molecule comprising a docking site, a toehold domain, and a hairpin domain, the hairpin domain comprising a fully or partially double-stranded stem domain and a loop domain, wherein the stem domain is complementary to a SNP-containing nucleic acid molecule, whereby, if present in the sample, the SNP-containing nucleic acid molecule will bind to and form a complex with the ultraspecific riboregulator, leaving a 3' region of the riboregulator in position to produce a reporter protein; and (b) performing an isothermal amplification to selectively amplify the SNP-containing nucleic acid molecule using a DNA polymerase and monomers. The SNP-containing nucleic acid molecule can be amplified using a SNP-specific forward primer, a SNP-specific blocking strand, a conventional reverse primer, a DNA polymerase, and monomers. The sample can be a biological sample. The biological sample can be a liquid sample. Detecting said SNP-containing nucleic acid molecule can be a positive or negative indicator of a disease-associated SNP in said sample. The toehold domain can be 2-6 nucleotides in length.

In another aspect, provided herein is a method for preferential amplification of a target DNA molecule comprising a mutation. The method can comprise or consist essentially of (a) contacting a comprising an oligonucleotide primer molecule and an oligonucleotide displacer molecule to a sample comprising a mutant DNA template, wherein the oligonucleotide primer molecule comprises a short forward toehold domain and a branch migration region at its 3' end, wherein the oligonucleotide displacer molecule comprises a short reverse toehold domain and a branch migration region at its 5' end, whereby the oligonucleotide primer and oligonucleotide displacer molecules associate with the mutant DNA template; and (b) contacting a DNA polymerase and monomers to the contacted sample of (a), wherein, in the presence of the mutant DNA template, the oligonucleotide primer completes a branch migration reaction to permit extension by the DNA polymerase and amplification of the mutant DNA template, and the oligonucleotide displacer completes a branch migration reaction that prevents extension by the DNA polymerase and amplification of a wild-type, non-mutated DNA template. In some cases, the method further comprises (c) repeating steps (a) and (b) along with a conventional amplification primer in the reverse direction until a desired degree of amplification of the target DNA molecule comprising the mutation is achieved. The oligonucleotide primer molecule can further comprise a docking site at its 5' end, and the oligonucleotide displacer molecule can comprise a docking site at its 3' end. The sample can be a biological sample. The biological sample can be a liquid sample. Detecting said target DNA molecule comprising a mutation can be a positive or negative indicator of a disease-associated mutation in said sample.

In a further aspect, provided herein is a SNP-specific primer and displacer system comprising an oligonucleotide primer molecule and an oligonucleotide displacer molecule, wherein the oligonucleotide primer molecule comprises a short forward toehold domain and a branch migration region at its 3' end, wherein the oligonucleotide displacer molecule comprises a short reverse toehold domain and a branch migration region at its 5' end and a domain at its 3' end that is not complementary to a DNA target molecule, and wherein the oligonucleotide primer molecule is complementary to a target DNA molecule and the oligonucleotide displacer molecule is complementary to a target DNA molecule comprising the wild-type sequence. Each of the oligonucleotide primer and oligonucleotide displacer molecules can further comprise a docking site. The forward toehold sequence can be 2-6 nucleotides in length. The reverse toehold sequence can be 2-6 nucleotides in length.

In another aspect, provided herein is an ultraspecific riboregulator, where the riboregulator is a synthetic nucleic acid molecule comprising a hairpin domain and a toehold domain, wherein the hairpin domain comprises a loop domain and a fully or partially double-stranded stem domain complementary to a target RNA molecule comprising a SNP mutation. The toehold sequence can be 2-5 nucleotides in length. The hairpin domain can further comprise a ribosomal binding site and a start codon, and the ultraspecific riboregulator can further comprise a detectable output gene.

In another aspect, provided herein is an ultraspecific riboregulator system comprising (a) a first riboregulator RNA molecule comprising a fully or partially double-stranded stem domain, a loop domain, a short toehold domain, and a coding sequence of a reporter gene, wherein the toehold and a portion of the stem is complementary to a target RNA molecule containing a SNP mutation, and (b) a second riboregulator RNA molecule comprising a fully or partially double-stranded stem domain a loop domain, and a short toehold domain, wherein the toehold and a portion of the stem is complementary to a target RNA molecule containing the wild-type sequence. The short toehold sequence can be 2-5 nucleotides in length.

In a further aspect, provided herein is a method for preferential amplification of a target DNA molecule comprising a SNP mutation. The method can comprise or consist essentially of (a) contacting a SNP-specific remote toehold primer to a sample comprising a target DNA molecule, wherein the SNP-specific remote toehold primer comprises (i) a 5' docking site complementary to the target DNA molecule, (ii) a spacer domain not complementary to the target DNA molecule, and (iii) a 3' mutant targeting remote toehold domain complementary to a target DNA molecule in a region comprising a SNP mutation, and whereby the SNP-specific remote toehold primer associates with the target DNA molecule; and (b) extending the mutant targeting hairpin of the SNP-specific remote toehold primer along the target DNA molecule with a DNA polymerase molecule and monomers to be incorporated into the extended remote toehold, using the target DNA molecule as a template, wherein, in the presence of the target DNA molecule comprising the SNP mutation, the mutant targeting remote toehold binds to the DNA template, leaving the 3' end in position to prime polymerization by the DNA polymerase molecule, and wherein, in the presence of the target DNA molecule not containing the SNP mutation, the remote toehold does not bind to the DNA template and prevents primer polymerization. In some cases, the method further comprises (c) repeating steps (a) and (b) along with a conventional amplification primer in the reverse direction until a desired degree of amplification of the target DNA molecule comprising a mutation is achieved. The remote toehold sequence can be 3-8 nucleotides in length. The sample can be a biological sample. The biological sample can be a liquid sample. Detecting said target DNA molecule comprising a mutation can be a positive or negative indicator of a disease-associated mutation in said sample.

In another aspect, provided herein is a method for preferential amplification of a target DNA molecule comprising a SNP mutation. The method can comprise or consist essentially of (a) contacting a SNP-specific intramolecular competitive primer to a sample comprising a target DNA molecule, wherein the SNP-specific intramolecular competitive primer comprises (i) a 5' wild-type targeting hairpin comprising a fully or partially double-stranded stem domain, a loop domain, and a short toehold domain, and (ii) a 3' mutant targeting hairpin comprising a fully or partially double-stranded stem domain complementary to a target DNA molecule comprising a SNP mutation, a loop domain, and a short toehold domain, wherein the wild-type targeting hairpin and the mutant targeting hairpin are separated by a spacer domain, and whereby the SNP-specific intramolecular competitive primer associates with the target DNA molecule; and (b) extending the mutant targeting hairpin of the SNP-specific intramolecular competitive primer along the target DNA molecule with a DNA polymerase molecule and monomers to be incorporated into the extended mutant targeting hairpin, using the target DNA molecule as a template, wherein, in the presence of the target DNA molecule comprising the SNP mutation, the mutant targeting hairpin binds to the DNA template, leaving the 3' end in position to prime polymerization by the DNA polymerase molecule, and wherein, in the presence of the target DNA molecule not containing the SNP mutation, the wild-type targeting hairpin binds to the DNA template and prevents primer polymerization by blocking its 3' end from binding to the DNA template. In some cases, the method further comprises (c) repeating steps (a) and (b) along with a conventional amplification primer in the reverse direction until a desired degree of amplification of the target DNA molecule comprising a mutation is achieved. The forward toehold sequence can be 2-6 nucleotides in length. The reverse toehold sequence can be 2-6 nucleotides in length. The sample can be a biological sample. The biological sample can be a liquid sample. Detecting said target DNA molecule comprising a mutation can be a positive or negative indicator of a disease-associated mutation in said sample.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

Figures 1A, 1B, 1C, 1D:
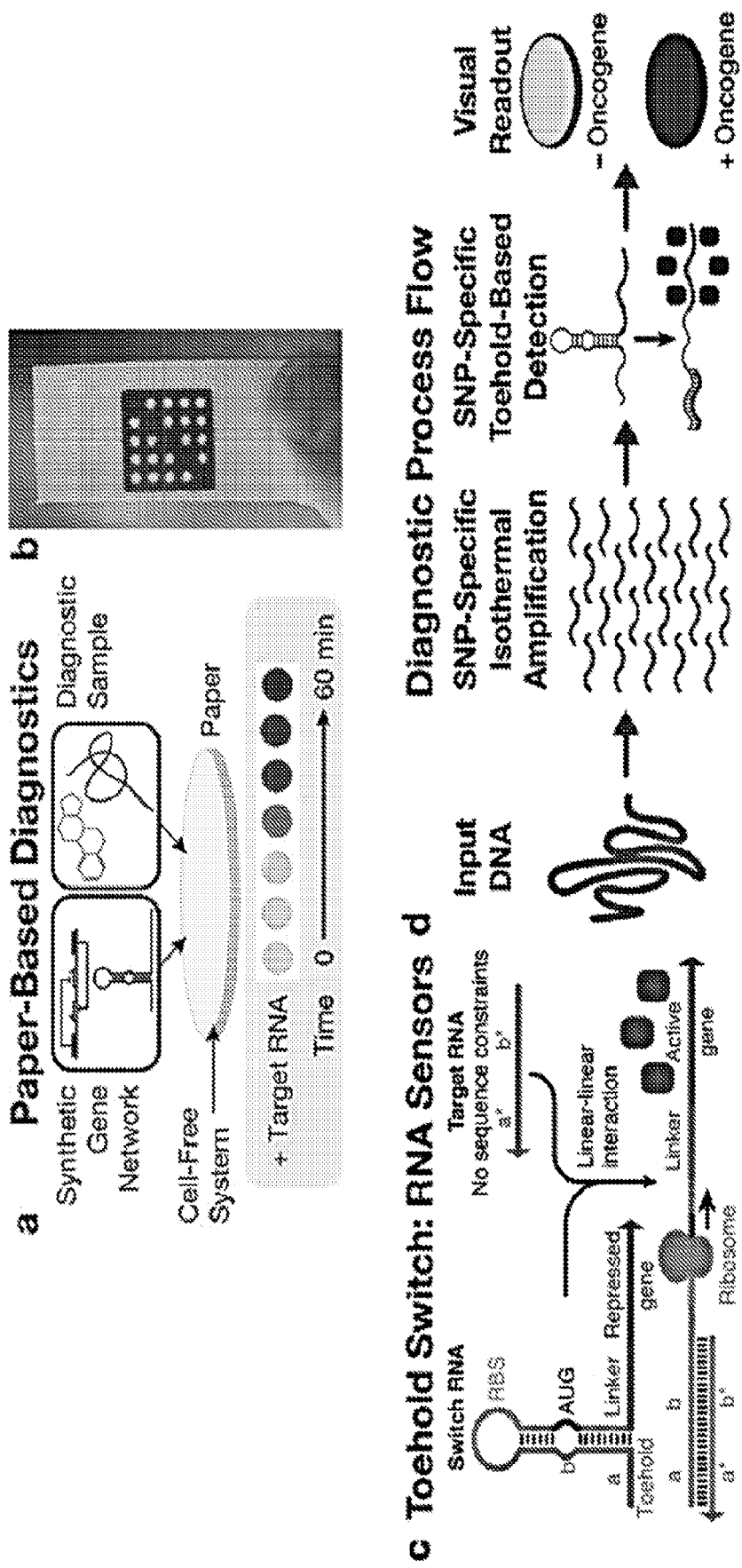
FIGS. 1A-1D illustrate an exemplary embodiment of the low-cost diagnostic systems described herein. (a) Cell-free systems are preserved on paper and reactivated with water. Bottom: Upon detection of a target nucleic acid, an enzymatic reaction yields a color change in under an hour. (b) Photograph of a paper-based device array. (c) Toehold switches are used to detect target RNAs and produce the reporter gene. They are computationally designed riboregulators that can output any protein of interest and detect arbitrary nucleic acids. (d) Flow of steps for a proposed diagnostic: input cell-free DNA (cfDNA) is amplified, detected in either DNA or RNA form, and yields a colorimetric result through an enzymatic reaction.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE DISCLOSURE

All publications, including but not limited to patents and patent applications, cited in this specification are herein incorporated by reference as though set forth in their entirety in the present application.

The methods and compositions provided herein are based at least in part on the inventors' development of effective strategies for rapid diagnostic tools based on specific detection of target nucleic acids. Simple, low-cost, and rapid diagnostic devices like home pregnancy tests and blood glucose meters have transformed healthcare over the past four decades, enabling people to monitor and take charge of their health in the comfort of their homes. Developing equivalent tests for cancer could enable people to seek treatment when the disease is in its early stages, or provide patients diagnosed with cancer the ability to monitor the disease as they undergo treatment. Accordingly, embodiments described herein relate to ultraspecific, programmable nucleic acid sensors that enable detection of a disease or condition (e.g., cancer, infection by a pathogen, rejection of a transplanted organ) using nucleic acids circulating in the blood in a few hours with minimal lab equipment and costs below $20 per test. These low-cost and potentially in-home DNA testing systems leverage emerging technologies for detecting infectious diseases in the developing world and could bring the costs of liquid biopsies down by over 100-fold. These systems promise to make liquid biopsies for early cancer screening widely available and enable routine monitoring of circulating cancer DNA, providing a wealth of information on treatment efficacy and the evolution of cancer in the body.

Without being bound to any particular theory or mechanism of action, it is believed that the inventors addressed limitations in the practical deployment of nucleic acid based molecular diagnostics by combining isothermal amplification methods with ultraspecific, programmable nucleic acid sensors capable of detecting a large diversity of target sequences. As described in the paragraphs and Examples that follow, the advantages of the ultraspecific nucleic acid sensors and methods provided herein are multifold and include, for example, transcription-only reactions that employ high dynamic range and can be integrated with existing amplification methods for one-pot amplification/detection reactions. Moreover, the ultraspecific nucleic acid sensors and methods provided herein provide SNP-specificity and can provide single-base resolution with greatly reduced reaction times.

Ultraspecific Nucleic Acid Sensors

Accordingly, in a first aspect, provided herein are ultraspecific, programmable nucleic acid sensors capable of binding to the target analyte for rapid, low-cost detection of nucleic acids associated with a disease or condition (e.g., cancer, infection by a pathogen, rejection of a transplanted organ) in a liquid biological sample. Embodiments described herein also relate to methods for construction of such nucleic acid sensors and methods for sequence-specific detection and amplification of disease-associated mutations, as well as testing systems for early screening and routine monitoring of circulating nucleic acids in liquid biological samples. As used herein, the terms "ultraspecific nucleic acid sensor" or "ultraspecific programmable nucleic acid sensor" refer to a synthetic nucleic acid molecule configured for specific detection of a target sequence (e.g., a wild-type nucleic acid sequence or a sequence comprising a single nucleotide polymorphism (SNP), where the sensor functions as a SNP-specific nucleic-acid-based toggle switch that regulates amplification of itself or another nucleic acid or production of a protein in response to a signaling (triggering) event. In cases in which the ultraspecific nucleic acid sensor produces a protein in response to a triggering event, the sensor can be referred to as an ultraspecific riboregulator. In some cases, the triggering event is detection of a cognate nucleic acid sequence.

Figure 9:
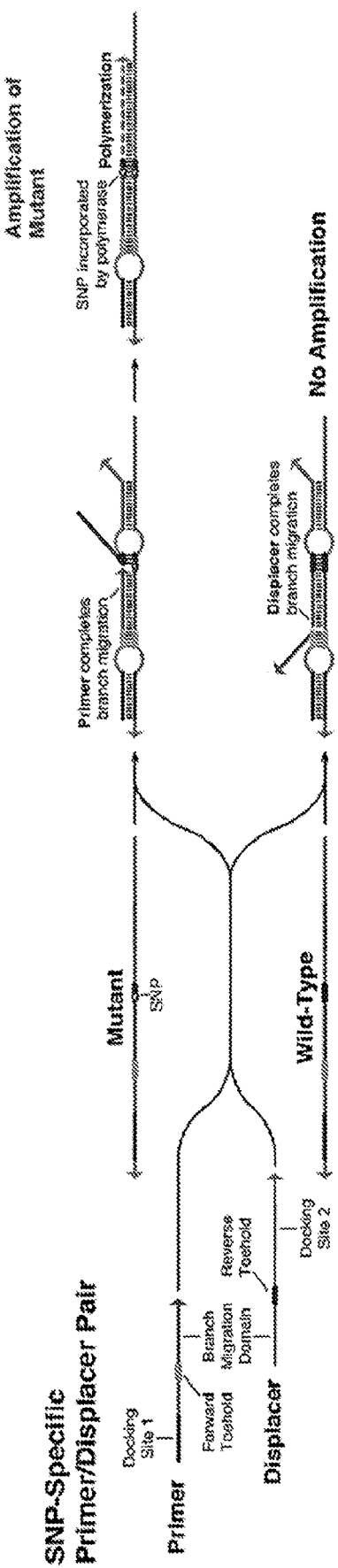
FIG. 9 describes SNP-specific primer/displacer pairs that employ a pair of DNA strands that compete for binding to the template to enable preferential amplification of mutant DNA templates. Both primer and displacer strands feature a docking site, short toehold domain, and branch migration region. For the mutant target, the primer strand completes a branch migration reaction to enable polymerization by DNA polymerase, while the displacer strand displaces the primer from the wild-type template to prevent polymerization.
Figure 10:
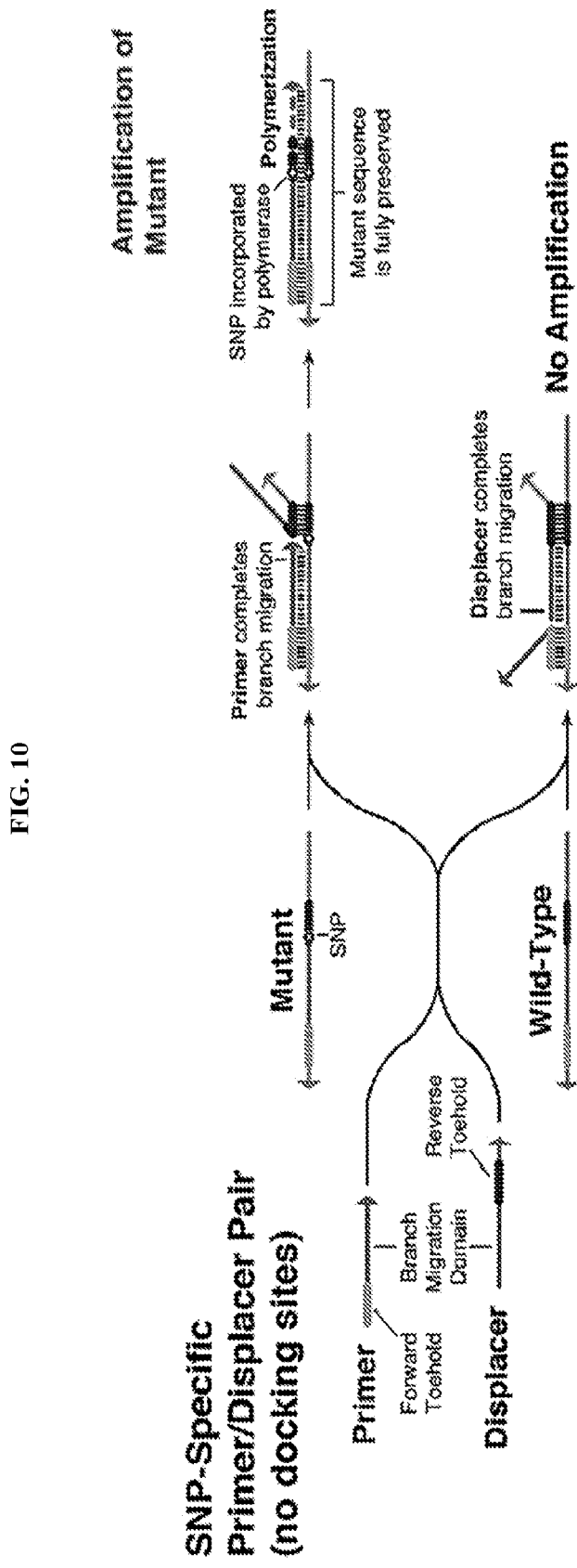
FIG. 10 describes SNP-specific primer/displacer pairs similar to those in FIG. 9, but without docking sites to encourage hybridization with the template. These systems enable specific amplification of the mutant template and do not cause any changes to the sequence of the DNA that is amplified.

In some cases, ultraspecific nucleic acid sensors of this disclosure include SNP-specific riboregulators (i.e., RNA-based systems in the disclosure that produce an output reporter protein; illustrated in FIGS. 1C-1D, 2A-2B, and 12), SNP-specific engineered DNA amplification primers that only prime polymerization with a SNP-containing sequence (illustrated in FIGS. 3, 5, 7), SNP-specific blockers that impede primer extension (illustrated in FIG. 4), and SNP-specific primer/displacer pairs (illustrated in FIGS. 9-10).

The term "liquid biological sample" as used herein will be understood to refer to a sample of biological fluid. Liquid biological samples include, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), washings of female reproductive tract, vaginal secretions, nasal secretions, cerebrospinal fluid (CSF), urine, feces, sputum, saliva, nasal mucous, prostate fluid, lavage, semen, lymphatic fluid, bile, tears, sweat, breast milk, breast fluid, the like or combinations thereof. In some cases, the liquid biological sample is prepared by removal of cells from a blood sample.

The liquid biological sample can be obtained from or provided by a subject by any appropriate means. As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "subject" is used herein interchangeably with "individual" or "patient."

As used herein, the terms "synthetic" and "engineered" are used interchangeably and refer to the aspect of having been manipulated by the hand of man.

As used herein, the terms "disease", "disease state", and "disorder" will be understood to include, but not be limited to, any acute or chronic pathological condition which could benefit from diagnosis and/or treatment. Accordingly, this disclosure provides ultraspecific nucleic acid sensors and methods of using such ultraspecific nucleic acid sensors to detect a nucleic acid sequence associated with a disease (e.g., a cancer) in a liquid biological sample of a subject (e.g., human) for the purpose of diagnosing and/or treating the disease.

Generally, the base design of the ultraspecific programmable nucleic acid sensors described herein was inspired by the toehold switch, a recently developed riboregulator. As used herein, the term "toehold switch" generally refers to a regulator of gene expression, configured to repress or activate translation of an open reading frame and thus production of a protein. Referring to the example illustrated in FIG. 1C, the binding of a cognate trigger RNA to a toehold switch activates gene translation downstream. The RNA stem-loop structure located upstream of the repressed output gene is responsible for sensing of the target RNA. The ribosomal binding site (RBS) and start codon for the output gene are positioned within the loop and within a bulge on the stem, respectively. When the trigger RNA binds to the single-stranded region at the 5' end (toehold), the stem will gradually unwind, and the RBS and the start codon will be exposed. As a result, the translation of the output gene will be activated.

Figures 2A, 2B:
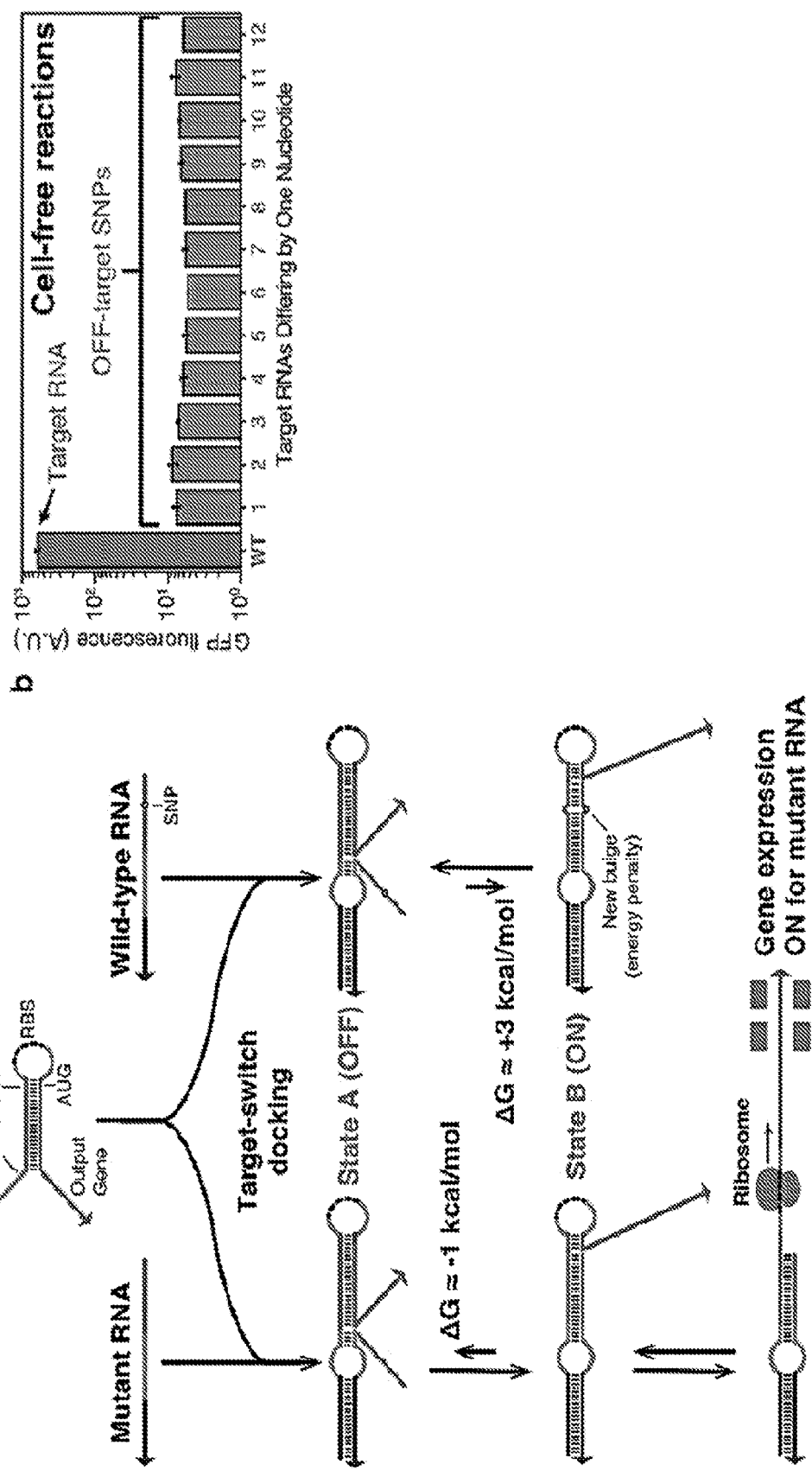
FIGS. 2A-2B illustrate the design and testing of exemplary single nucleotide polymorphism (SNP)-specific riboregulators. (a) Design schematic showing the origin of SNP-specificity through small energy differences. (b) Testing of the riboregulators in cell-free reactions. Only target RNA shows a strong response with low expression for 12 targets containing SNPs.

Referring now to FIG. 2A, which illustrates an exemplary ultraspecific programmable nucleic acid sensor (also referred to herein as a "SNP-specific riboregulator), sensors of this disclosure are synthetic nucleic acid molecules comprising (a) a docking site, (b) one or more toehold domains, (c) a fully or partially double-stranded stem-forming domain, and (d) a loop-forming domain, wherein at least a portion of the synthetic nucleic acid molecule is complementary to a target nucleic acid sequence. In certain embodiments, the toehold domains are short, having a length of 2-8 (e.g., 2, 3, 4, 5, 6, 7, 8) nucleotides (nt). In some cases, the loop-forming domain comprises a ribosomal binding site (RBS). In some cases, the SNP-specific riboregulator further comprises (e) an output nucleotide sequence such as a sequence encoding a molecule that generates a detectable product such as a fluorescent signal (e.g., Green Fluorescent Protein (GFP) or fluorescent variant thereof) or a colorimetric signal.

Without being bound to any particular theory or mechanism of action, the design of ultraspecific programmable nucleic acid sensors exploit very subtle changes in thermodynamics that occur when a base pair is broken within an RNA duplex. Each broken base pair within a duplex generates a free energy penalty of ~4 kcal/mol. To exploit these thermodynamics, a sensor is designed to have slightly negative free energy (−1 kcal/mol) upon binding to its cognate mutant RNA and transitioning from state A to the favorable state B (see FIG. 2A). Once the system reaches favorable state B, the sensor begins to translate detectable reporters as the ribosomal binding site (RBS) and start codon (AUG) are readily exposed by spontaneous breaking of the weak duplex surrounding the RBS. When a nucleic acid molecule comprising a SNP is present, the equilibrium between states A and state B is shifted as a result of the new bulge in the state B RNA duplex. This single bulge yields a free energy of +3 kcal/mol and, thus, makes state A the most probable configuration of the SNP-specific sensor. In state A, the RBS and start codon of the switch RNA are sequestered within the stem of the hairpin and are unable to be translated. The subtle thermodynamics of the SNP-specific sensor are enabled by a docking site in the switch RNA, which places both the switch RNA and target RNA in close proximity to enable weak interactions between short, 2-6 nucleotide (nt) regions to occur (see, for example, FIG. 2A in toehold domains). When tested in vivo (in E. coli) and in vitro (see FIG. 2B), the SNP-specific riboregulators provided up to 100-fold greater response synthetic target RNAs in both contexts compared to targets with SNPs.

In some cases, the ultraspecific programmable nucleic acid sensors are SNP-specific riboregulators useful for the detection of oncogenes. For example, the sensors can be designed to detect target oncogenes with single-nucleotide resolution using an isothermal amplification reaction. SNP-specific riboregulators that specifically target oncogenes generated from SNPs were designed in silico. Of particular interest are riboregulators configured for detection of SNPs known to occur frequently in colorectal cancer in genes such as KRAS (KRAS proto-oncogene, GTPase), NRAS (NRAS proto-oncogene, GTPase), BRAF (B-Raf proto-oncogene, serine/threonine kinase), and EGFR (epidermal growth factor receptor, tyrosine kinase), or other members of the Ras, Raf, and receptor tyrosine kinase families. KRAS and NRAS encode proteins belonging to the Ras family of oncogenes. BRAF encodes a protein belonging to the RAF family of serine/threonine protein kinases.

In some cases, it may be advantageous to use "flattening" RNA strands that bind around the target RNA recognition site to remove secondary structure of the target RNAs that may prevent riboregulators from activating. For oncogenes with insertions or deletions, the ultraspecific programmable nucleic acid sensors described herein should accommodate these mutations since they incur a similar energy penalty as a SNP.

Figure 3:
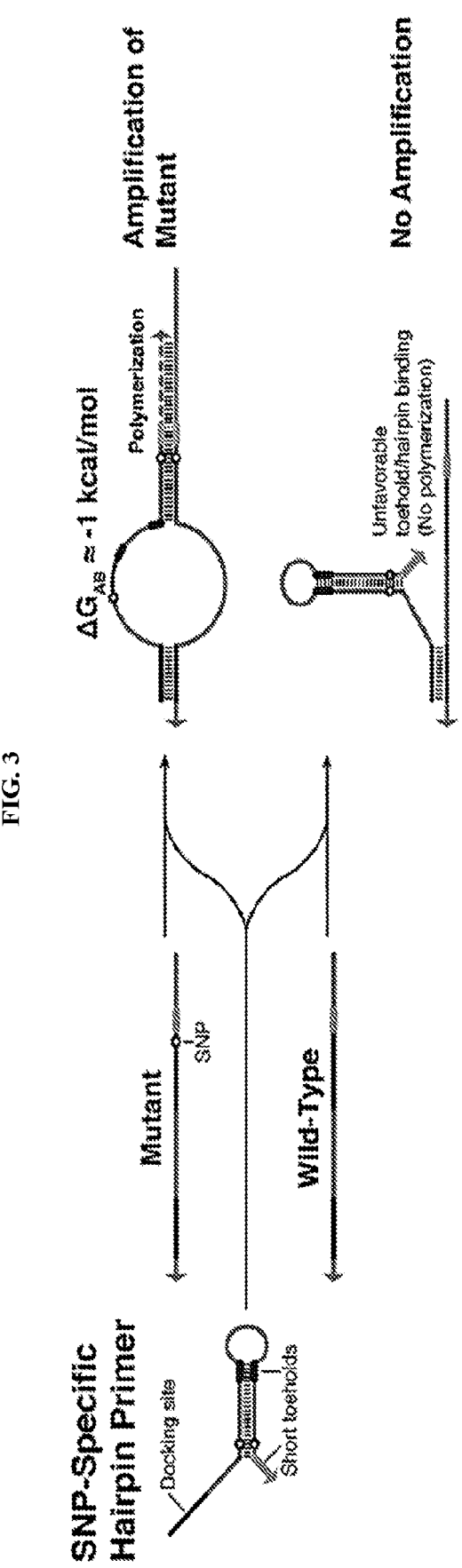
FIG. 3 describes SNP-specific hairpin primers that feature a docking site and a hairpin with a short toehold at the 3' end. The docking site is used to bind with high affinity to the mutant and wild-type templates while the hairpin establishes SNP-specific primer hybridization to the mutant template.

In some cases, the ultraspecific programmable nucleic acid sensor is a SNP-specific engineered DNA amplification primer that only primes with a SNP-containing sequence. In certain embodiments, the SNP-specific primer comprises (a) a docking site, (b) one or more toehold domains, (c) a fully or partially double-stranded stem-forming domain, and (d) a loop-forming domain, wherein at least a portion of the synthetic nucleic acid molecule is complementary to a target nucleic acid sequence comprising a SNP of interest. In certain embodiments, the toehold domains are short, 2-6 nucleotide (nt) regions. Referring to FIG. 3, an exemplary SNP-specific engineered amplification primer comprises a docking site and a hairpin with a short toehold at the 3' end. Preferably, SNP-specific engineered amplification primers feature single-stranded docking sites having melting temperatures of approximately 37° C., designed for initial binding to the template DNA. The docking site is used to bind with high affinity to the mutant and wild-type templates, while the engineered amplification primer establishes SNP-specific primer hybridization to the mutant template. The hairpin structure will only bind favorably to a template with perfect complementarity. In such cases, binding to the template leaves the 3' end in position to prime polymerization using the DNA polymerase. This free energy balancing approach should apply to a range of temperatures. Accordingly, in the presence of a SNP-containing nucleic acid molecule, the toehold and docking regions of the SNP-specific primer form an energetically favorable complex and polymerization occurs, thus amplifying the SNP-containing molecule.

Figure 4:
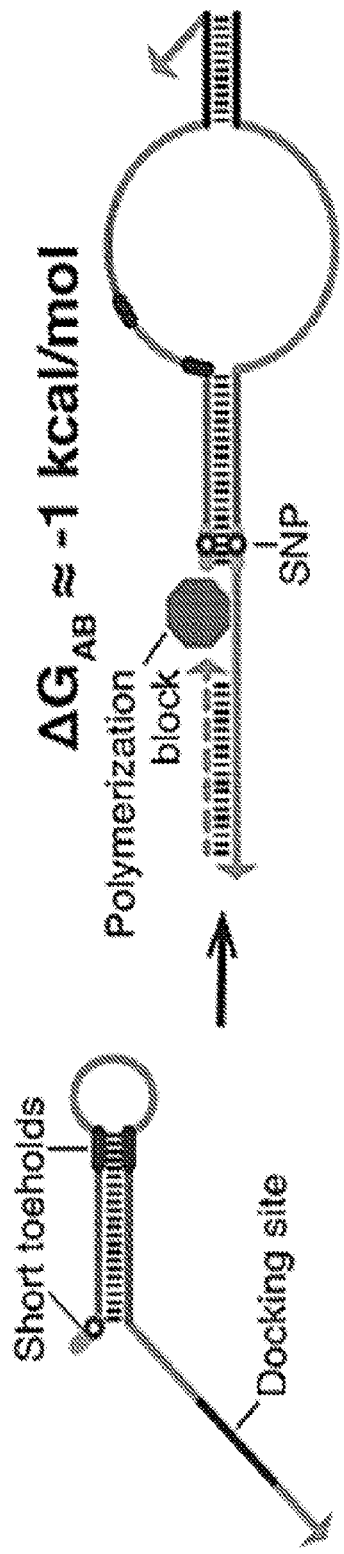
FIG. 4 describes SNP-specific blocking strands that comprise a docking site and a hairpin with a short toehold at the 5' end. The docking site binds to both the mutant and wild-type templates while the hairpin binds in a SNP-specific fashion to a template that should not be amplified. The hybridization of the blocker strand hairpin is used to inhibit primer extension by the DNA polymerase. The 3' end of the blocking strand is designed to not bind to the template to ensure it does not undergo polymerization.

In some cases, an ultraspecific programmable nucleic acid sensor is a SNP-specific blocking strand or "blocker" configured to impede primer extension in a SNP-specific manner. The SNP-specific blocking strand is a synthetic nucleic acid molecule comprising (a) a docking site, (b) a hairpin domain comprising a fully or partially double-stranded stem-forming domain, and a loop-forming domain, and (c) one or more toehold domains, wherein at least one of the toehold domains is located at the 5' end of the synthetic nucleic acid molecule. As illustrated in FIG. 4, the docking site binds to both the mutant and wild-type templates, while the hairpin binds in a SNP-specific fashion to a template that should not be amplified. The hybridization of the blocking strand hairpin is used to inhibit primer extension by the DNA polymerase. The 3' end of the blocking strand is designed to not bind to the template to ensure it does not undergo polymerization. Preferably, blocking strands feature single-stranded docking sites having melting temperatures of approximately 37° C., designed for initial binding to the template DNA, and a hairpin structure that will only bind favorably to a template with perfect complementarity. For SNP-specific blocking strands, binding to the template leaves the docking strand 3' end unpaired and a long base-paired stretch toward the 5' end that should obstruct amplification of wild-type templates (FIG. 4). This free energy balancing approach should apply to a range of temperatures.

Figure 5:
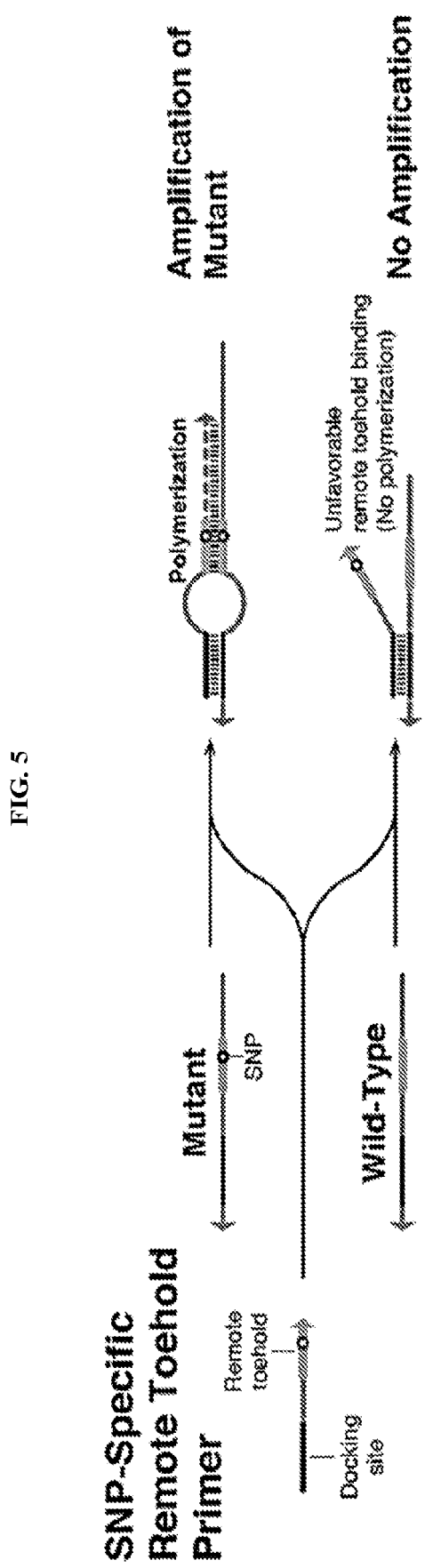
FIG. 5 describes SNP-specific remote toehold primers that feature a docking site and a short toehold domain at the 3' end. The docking site is used to bind with high affinity to the mutant and wild-type templates. The binding of the short remote toehold is very sensitive to mismatches, which enables it to bind with high affinity only to the mutant template with a known SNP.

In some cases, an ultraspecific programmable nucleic acid sensor is a SNP-specific remote toehold primer. Referring to FIG. 5, SNP-specific remote toehold primers comprise (a) a docking site and (b) a short toehold domain at the 3' end of the synthetic nucleic acid molecule. In such cases, the ultraspecific programmable nucleic acid sensor does not comprise a hairpin region. As illustrated in FIG. 5, the docking site binds with high affinity to both the mutant and wild-type templates, while the short toehold domain is very sensitive to mismatches and binds with high affinity only to the mutant template comprising a known SNP. In the presence of a template comprising a known SNP, binding of the SNP-specific remote toehold primer to the template leaves the 3' end in position to prime polymerization using the DNA polymerase. Accordingly, in the presence of a SNP-containing template, the toehold and docking regions of the SNP-specific remote toehold primer form an energetically favorable complex and polymerization occurs, thus amplifying the SNP-containing molecule. In the presence of only wild-type templates (i.e., templates lacking the SNP or other mutation), amplification does not occur since the 3' end of the primer does not hybridize with the template.

Figure 7:
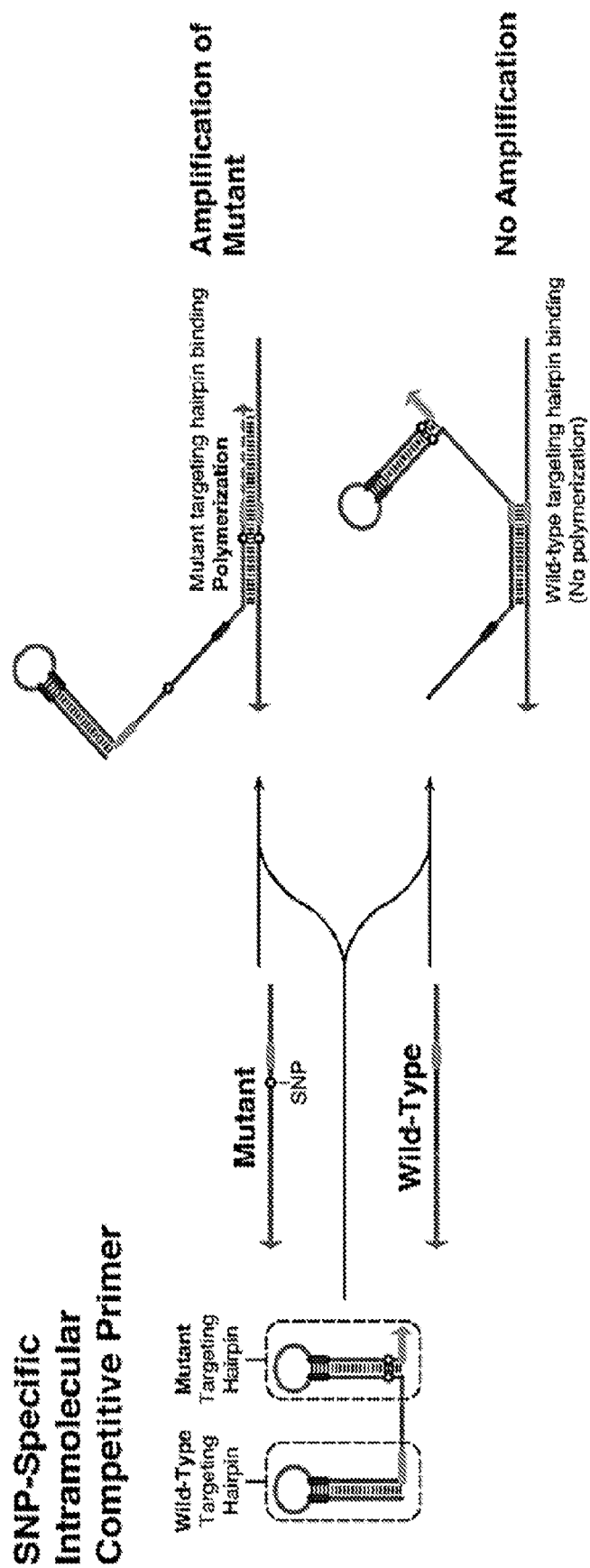
FIG. 7 describes SNP-specific intramolecular competitive primers that consist of two hairpins separated by a spacer domain. Each hairpin is designed to bind to either the mutant or wild-type template and can thus compete for binding to each template. If the hairpin located at the 3' end of the primer successfully hybridizes with the mutant template, primer extension can occur.

In certain embodiments, an ultraspecific programmable nucleic acid sensor is a SNP-specific intramolecular competitive primer. As illustrated in FIG. 7, such a SNP-specific intramolecular competitive primer can comprise (a) a wild-type targeting hairpin and (b) a mutant targeting hairpin, wherein each hairpin comprises a 3' short toehold domain. In some cases, the wild-type targeting hairpin is 5' to the mutant targeting hairpin. In other cases, the wild-type targeting hairpin is 3' to the mutant targeting hairpin. The mutant targeting hairpin portion of the sensor is configured to bind with high affinity to a SNP-containing template. In the case where the primer has the mutant targeting hairpin in the 3' position, binding to the template leaves the 3' end in position to prime polymerization using the DNA polymerase and polymerization occurs, thus amplifying the SNP-containing molecule.

When used in an isothermal amplification reaction, SNP-specific DNA amplification primers (illustrated in FIGS. 3, 5, and 7 and described in the paragraphs above) bind to a target DNA molecule in its single-stranded form and are used in conjunction with a conventional a reverse DNA primer that can be added to the reaction to generate DNA copies. As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of DNA. A "reverse primer" is complementary to the sense-strand of DNA.

In certain embodiments, an ultraspecific programmable nucleic acid sensor comprises a set of two nucleic acid strands: an oligonucleotide primer ("primer strand") and an oligonucleotide displacer ("displacer strand"). The oligonucleotide primer/displacer pair is configured for SNP-specific template amplification. Referring to FIG. 9, a SNP-specific primer/displacer pair comprises a pair of DNA strands that compete for binding to the template to enable preferential amplification of mutant DNA templates. Each strand (the primer strand and the displacer strand) features a docking site, a short toehold domain (e.g., 2-6 nucleotides), and branch migration region. The docking site, toehold, and branch migration domain of the primer strand are perfectly complementary to both the on-target and off-target templates (mutant and wild-type templates, respectively, in FIG. 9). In some cases, the strands feature a docking site, a spacer domain of 5 to 15 nts or more in length, a short toehold domain of 2 to 10 nts in length, and a branch migration domain of 8 to 20 nts or more in length; however, these domains occur in the opposite order in the two strands. In addition, the displacer strand features a 3' domain of 4 to 15 nts in length that is designed to not hybridize with the template, thus preventing polymerization and amplification of the displacer. In the displacer strand, the toehold domain is only complementary to the off-target template and establishes the SNP-specificity of the primer/displacer system. Branch migration is a process that occurs when two nucleic acid strands compete for binding to the same complementary nucleic acid template and, in the process, causes one of the competing strands to be displaced from the template. The primer/displacer pair is designed such that the displacer strand will outcompete the primer for binding to a wild-type template and thereby complete a branch migration. Conversely, the primer will outcompete the displacer for binding to a SNP template, complete the branch migration, and enable polymerization by DNA polymerase.

Oligonucleotide primer/displacer pairs as described herein are particularly suited for preferential amplification of a target DNA molecule comprising a mutation. In certain embodiments, the method comprises (a) contacting a comprising an oligonucleotide primer molecule and an oligonucleotide displacer molecule to a sample comprising a mutant DNA template, wherein the oligonucleotide primer molecule comprises a short forward toehold domain and a branch migration region at its 3' end, wherein the oligonucleotide displacer molecule comprises a short reverse toehold domain and a branch migration region at its 5' end, whereby the oligonucleotide primer and oligonucleotide displacer molecules associate with the mutant DNA template (illustrated in FIG. 10); and (b) contacting a DNA polymerase and monomers (e.g., nucleotide monomers) to the contacted sample of (a), wherein, in the presence of the mutant DNA template, the oligonucleotide primer completes a branch migration reaction to permit extension by the DNA polymerase and amplification of the mutant DNA template, and the oligonucleotide displacer completes a branch migration reaction that prevents extension by the DNA polymerase and amplification of a wild-type, non-mutated DNA template.

As used herein, the term "nucleotide" or "nucleotide moiety" refers to a sub-unit of a nucleic acid (whether DNA or RNA or analogue thereof) which includes a phosphate group, a sugar group and a heterocyclic base, as well as analogs of such sub-units. A "nucleotide monomer" refers to a molecule which is not incorporated in a larger oligo- or poly-nucleotide chain and which corresponds to a single nucleotide sub-unit. In some cases, other groups (e.g., protecting groups) can be attached to any component(s) of a nucleotide or nucleotide monomer.

A "nucleoside" or "nucleoside moiety" refers to a nucleic acid subunit including a sugar group and a heterocyclic base, as well as analogs of such sub-units. Other groups (e.g., protecting groups) can be attached to any component(s) of a nucleoside. A "nucleoside residue" refers to a molecule having a sugar group and a nitrogen containing base (as in a nucleoside) as a portion of a larger molecule, such as in a polynucleotide, oligonucleotide, or nucleoside phosphoramidite.

As used herein, the terms "nucleic acid polymer" or "nucleic acids" refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), as well as other hybridizing nucleic-acid-like molecules such as those with substituted backbones, e.g., peptide nucleic acids (PNAs) or other nucleic acids comprising modified bases and sugars. In some cases, the target nucleic acid is a double stranded DNA. In some cases, the target nucleic acid is cell-free DNA (cfDNA). However, the methods of the invention are not limited to double stranded DNA because other nucleic acid molecules, such as a single stranded DNA or RNA can be turned into double stranded DNA by one of skill in the arts using known methods. Suitable double stranded target DNA may be a genomic DNA or a cDNA.

Nucleic acids and/or other moieties of the invention may be isolated. As used herein, "isolated" means to separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Methods

In another aspect, provided herein is a method of selectively detecting a target DNA molecule containing a SNP or other mutation of interest. In certain embodiments, the method for detecting a SNP-containing DNA molecule in a sample comprises (a) contacting an ultraspecific riboregulator to a sample, where the riboregulator is a synthetic nucleic acid molecule comprising a docking site, a toehold domain, and a hairpin domain comprising a fully or partially double-stranded stem domain and a loop domain, where the stem domain is complementary to a SNP-containing RNA molecule, whereby, if present in the sample, the SNP-specific RNA molecule will bind to and form a complex with the ultraspecific riboregulator, leaving a 3' portion of the riboregulator in position produce a reporter gene; and (b) performing an isothermal amplification to selectively amplify the SNP-containing DNA molecule using a DNA polymerase and monomers. In some cases, the SNP-containing DNA molecule is amplified by isothermal amplification using, for example, a SNP-specific forward primer, a SNP-specific blocking strand, a conventional reverse primer, a DNA polymerase, and monomers; or in another example, SNP-specific primer and displacer strands, a conventional reverse primer, a DNA polymerase, and monomers. Where the SNP is a cancer-associated SNP, detecting a SNP-specific DNA molecule in a sample (e.g., a liquid biological sample) is a positive or negative indicator of a cancer-associated SNP in the sample.

In some cases, the method is for preferential amplification of a target DNA molecule comprising a mutation (i.e., a mutant template), where the method comprises (a) contacting an oligonucleotide primer and an oligonucleotide displacer molecule to a sample comprising a single-stranded target DNA molecule, wherein the oligonucleotide primer molecule comprises a short forward toehold domain and a branch migration region at its 3' end, wherein the oligonucleotide displacer molecule comprises a short reverse toehold domain and a branch migration region at its 5' end, whereby the oligonucleotide primer and displacer molecules associate with a single-stranded target DNA molecule; (b) contacting a DNA polymerase and monomers to the contacted sample of (a). In the presence of the mutant DNA template, the oligonucleotide primer completes a branch migration reaction to permit extension by the DNA polymerase and amplification of the mutant DNA template, and the oligonucleotide displacer completes a branch migration reaction that prevents extension by the DNA polymerase and amplification of a wild-type, non-mutated DNA template. By including a conventional reverse primer in a nucleic acid amplification reaction, these interactions between the target DNA, primer, and displacer can be repeated until a desired degree of amplification of the DNA molecule comprising a mutation is achieved.

In other cases, the method for preferential amplification of a target DNA molecule comprising a SNP mutation comprises: contacting a SNP-specific intramolecular competitive primer to a sample comprising a target DNA molecule, wherein the SNP-specific intramolecular competitive primer comprises (i) a 5' wild-type targeting hairpin comprising a fully or partially double-stranded stem domain, a loop domain, and a short toehold domain, and (ii) a 3' mutant targeting hairpin comprising a fully or partially double-stranded stem domain complementary to a target DNA molecule comprising a SNP mutation, a loop domain, and a short toehold domain, wherein the wild-type targeting hairpin and the mutant targeting hairpin are separated by a spacer domain, and whereby the SNP-specific intramolecular competitive primer associates with the target DNA molecule; and (b) extending the mutant targeting hairpin of the SNP-specific intramolecular competitive primer along the target DNA molecule with a DNA polymerase molecule and monomers to be incorporated into the extended mutant targeting hairpin, using the target DNA molecule as a template, where, in the presence of the target DNA molecule comprising the SNP mutation, the mutant targeting hairpin binds to the DNA template, leaving the 3' end in position to prime polymerization by the DNA polymerase molecule, and where, in the presence of the target DNA molecule not containing the SNP mutation, the wild-type targeting hairpin binds to the DNA template and prevents primer polymerization by blocking its 3' end from binding to the DNA template. By adding a conventional reverse primer in a nucleic acid amplification reaction, the interactions between the target DNA and intramolecular competitive primer can be repeated until a desired degree of amplification of the double-stranded target DNA molecule comprising a mutation is achieved.

In some cases, the method comprises an isothermal nucleic acid amplification technique. Isothermal amplification reactions generally comprise one or more enzymes that disrupt base pairing in double-stranded DNA templates to allow primers, displacers, and/or blockers to bind to exposed single-stranded DNA regions. In certain embodiments, the isothermal nucleic acid amplification technique is Recombinase-Polymerase Amplification (RPA), which is a method for the amplification of target nucleic acid polymers without the need for thermal melting of double-stranded templates. RPA employs polymerases (DNA polymerases or polymerase complexes capable of strand displacement) to generate copies of template nucleic acid molecules. It is a necessity of most nucleic acid polymerases that incorporation requires a free 3'-hydroxyl moiety on the terminal sugar of a short stretch of double-stranded nucleic acid adjacent to the site of new synthesis. This stretch of double-stranded nucleic acid is typically formed on a template by a short complementary sequence, called a primer, which serves as an initiation site for the polymerase synthesis reaction. Typically, for in vitro reactions the primer is supplied as a short, often chemically synthesized, single-stranded DNA (or modified DNA or RNA), and is usually referred to as an oligonucleotide primer. For the methods provided herein, primers can be designed to specifically target a gene of interest such as a gene of a particular pathogen or a cancer marker.

The ability of RPA to discriminate between target and non-target DNA and amplify only target sequences is a key aspect of improved sensitivity. For the purposes of this disclosure, each of the terms "target" and non-target" can refer to a wild-type or mutant (e.g., SNP-containing) nucleic acid molecule, depending on the intended target of the method. For example, the target may be a SNP-containing nucleic acid molecule if the method is employed to detect the presence of a SNP in a sample.

While RPA is exemplified herein, any isothermal amplification protocol can be used according to the methods provided herein. For example, other isothermal amplification methods include NASBA (nucleic acid sequence-based amplification), loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), and single primer isothermal amplification (SPIA). In some cases, recombinase polymerase amplification (RPA) is used with the "one-pot" amplification and detection methods provided herein. In such cases, the methods comprise performing reverse transcription (RT), RPA, and transcription (TX) methods in a single test tube. In other cases, LAMP (loop-mediated isothermal amplification) is performed.

The terms "detect" or "detection" as used herein indicate the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

The methods provided herein can detect virtually any pathogen, genetic mutation, or foreign DNA (e.g., from an organ transplant) for which genetic information (e.g., gene sequences) is available. By way of example, pathogens may comprise viruses including, without limitation, flaviruses, human immunodeficiency virus (HIV), Ebola virus, single stranded RNA viruses, single stranded DNA viruses, double-stranded RNA viruses, double-stranded DNA viruses. Other pathogens include but are not limited to parasites (e.g., malaria parasites and other protozoan and metazoan pathogens (*Plasmodia* species, *Leishmania* species, *Schistosoma* species, *Trypanosoma* species)), bacteria (e.g., *Mycobacteria*, in particular, *M. tuberculosis, Salmonella, Streptococci, E. coli, Staphylococci*), fungi (e.g., *Candida* species, *Aspergillus* species, *Pneumocystis jirovecii* and other *Pneumocystis* species), and prions.

In certain embodiments, the methods detect viruses including, without limitation, the human-pathogenic flaviviruses such Zika virus (e.g., Zika strain from the Americas, ZIKV), yellow fever virus, and dengue virus serotypes 1 (DENV1) and 3(DENV3), and closely related viruses such as the chikungunya virus (CHIKV). In other embodiments, the methods detect negative-stranded RNA viruses such as Ebola virus and positive-stranded RNA viruses, such as viruses of the family Caliciviridae (e.g., human enteric viruses such as norovirus and sapovirus). As described in the Examples, the methods in some cases employ SNP-specific sensors to detect target nucleic acids derived from viral genomes. Specifically, the steps for detecting the presence of viral nucleic acids comprise isothermal amplification. In some cases, the isothermal amplification is NASBA (nucleic acid sequence-based amplification). The three enzymes involved in a NASBA reaction are a reverse transcriptase, RNase H, and T7 RNA polymerase. The amplification process begins with binding of the NASBA reverse primer to a target RNA, and an RNA/DNA duplex is created by reverse transcription. The RNA template is then degraded by RNase H which only targets RNA in RNA/DNA duplex, but not single-stranded RNA (target RNA). Now the single-stranded DNA is ready for the binding of the forward NASBA primer containing the T7 promoter for the elongation of the complementary strand. Finally, T7-mediated transcription of the double-stranded DNA templates creates copies of the target RNA sequence.

As used herein, a "sample" means any material that contains, or potentially contains, which could be infected or contaminated by the presence of a pathogenic microorganism. Samples appropriate for use according to the methods provided herein include biological samples such as, for example, blood, plasma, serum, urine, saliva, tissues, cells, organs, organisms or portions thereof (e.g., mosquitoes, bacteria, plants or plant material), patient samples (e.g., feces or body fluids, such as urine, blood, serum, plasma, or cerebrospinal fluid), food samples, drinking water, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples. In other embodiments, the methods provided herein are used for anti-counterfeit applications, such as confirming that pharmaceuticals are genuine or confirming the identity of high value items that have been fabricated or are known to contain specific nucleic acid species.

In certain embodiments, SNP-specific riboregulators and isothermal amplification are integrated for low-cost oncogene detection. For example, the SNP-specific riboregulator design and isothermal amplification protocols described herein can be integrated to enable detection of oncogenes via known SNPs or foreign genetic material from transplanted tissue or organs. In some cases, amplifications in liquid-phase reactions are performed, and then liquid from these reactions are added to paper-based riboregulator sensors. If liquid-phase reactions are successful, amplifications can be performed on the paper substrates. Microfluidic channels can be defined using a wax printer. These channels can be optimized ensure that reactions are sent to the riboregulator assay after sufficient amplification has occurred. In an alternative approach, the amplification and readout are performed on separate pieces of paper. For example, samples can be added to the amplification assay and left at 37° C. in either an incubator or by affixing to the body. After sufficient amplification time (typically 30 minutes to 2 hours), the riboregulator substrate is placed atop the amplification substrate and water is added to the upper cell-free wells. Capillary forces facilitate transfer the amplification product into the reporter reactions. Assay results are read out from the top set of reactions using, for example, a plate reader or a custom smartphone app.

In some cases, the device comprises a preserved paper test article, upon which any step(s) of the method provided herein can be performed. In preferred embodiments, the paper test article is preserved by freeze-drying, the SNP-specific sensors and methods provided herein can be performed for clinical application at a cost of less than $1 per assay and do not require translation to produce reporters for the diagnostic test. In other embodiments, the enzymes and DNA encoding the SNP-specific sensors can be freeze-dried in test tubes to render them stable at room temperature. These freeze-dried components can be reactivated upon addition of a sample and water, and can report on the presence of an endogenous nucleic acid of interest in the sample.

In some cases, the device is used with a portable electronic reader. In this manner, the electronic reader serves as companion technology that provides robust and quantitative measurements of device outputs. An exemplary electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of signal output, an acrylic chip that holds the freeze-dried, paper-based reactions or test tube reactions is placed into the reader between an LED light source (e.g., 470 nm or 570 nm), electronic sensors, and one or more optical filters as necessary. Using onboard electronics, samples can be read at a rate of 29 reads per minute. Accordingly, the portable electronic reader provides low-noise measurements of changes associated with the reporter element including changes in light transmission due to, for example, an enzyme-mediated color change or fluorescence. Portable electronic readers can also be used to detect optical changes in samples processed in test tubes.

Articles of Manufacture

In another aspect, provided herein are articles of manufacture useful for detecting and/or preferentially amplifying a SNP-specific nucleic acid, including infection-associated or disease-associated SNPs (e.g., cancer associated) and foreign nucleic acids (e.g., from an organ transplant). In certain embodiments, the article of manufacture is a kit for detecting a pathogen, where the kit comprises a plurality of preserved paper test or test tube test articles and an electronic optical reader. Optionally, a kit can further include instructions for performing the detection and/or amplification methods provided herein.

In certain embodiments, provided herein are paper-based or test tube-based articles of manufacture comprising freeze-dried or lyophilized amplification reagents and buffer components. For such embodiments, the paper-based or test tube-based articles of manufacture provide one-pot reactions that simply require rehydration for use as low-cost diagnostic tests that are appropriate for use in the field as well as in clinical settings. In certain of these embodiments, the paper-based or test tube-based articles of manufacture are provided with instructions for rehydrating the amplification and buffer components for use of the materials as diagnostic tests.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

So that the compositions, methods, and systems provided herein may more readily be understood, certain terms are defined:

As used in this specification and the appended claims, the singular forms "a," "an," and "the" include plural references and, unless clearly indicated to the contrary, should be understood to mean "at least one." Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, "about" means within 5% of a stated amount or concentration range or within 5% of a stated time frame.

It should also be understood that, unless clearly indicated to the contrary, in any methods claimed herein that include more than one step or act, the order of the steps or acts of the method is not necessarily limited to the order in which the steps or acts of the method are recited.

Having now described the invention, the same will be illustrated with reference to certain examples, which are included herein for illustration purposes only, and which are not intended to be limiting.

EXAMPLES

SNP-Specific Remote Toehold Primers

Remote toehold primers provide enhanced sequence specificity by coupling an extended docking site with a short remote toehold domain whose binding is sensitive to single-nucleotide changes in the template as illustrated in FIG. 5. In these primers, the 5' docking site binds to both the mutated and wild-type targets and the remote toehold domain is separated from the docking site by a spacer of 5 to 15 nts or more. The remote toehold on the 3' end of the primer is designed to be complementary to the SNP-containing region of the template and will thus bind to the on-target mutated template to enable extension by the DNA polymerase. With the off-target wild-type template, a single mismatch in hybridization with the remote toehold prevents the 3' end of the primer from binding and disrupts primer extension by the DNA polymerase.

Figure 6:
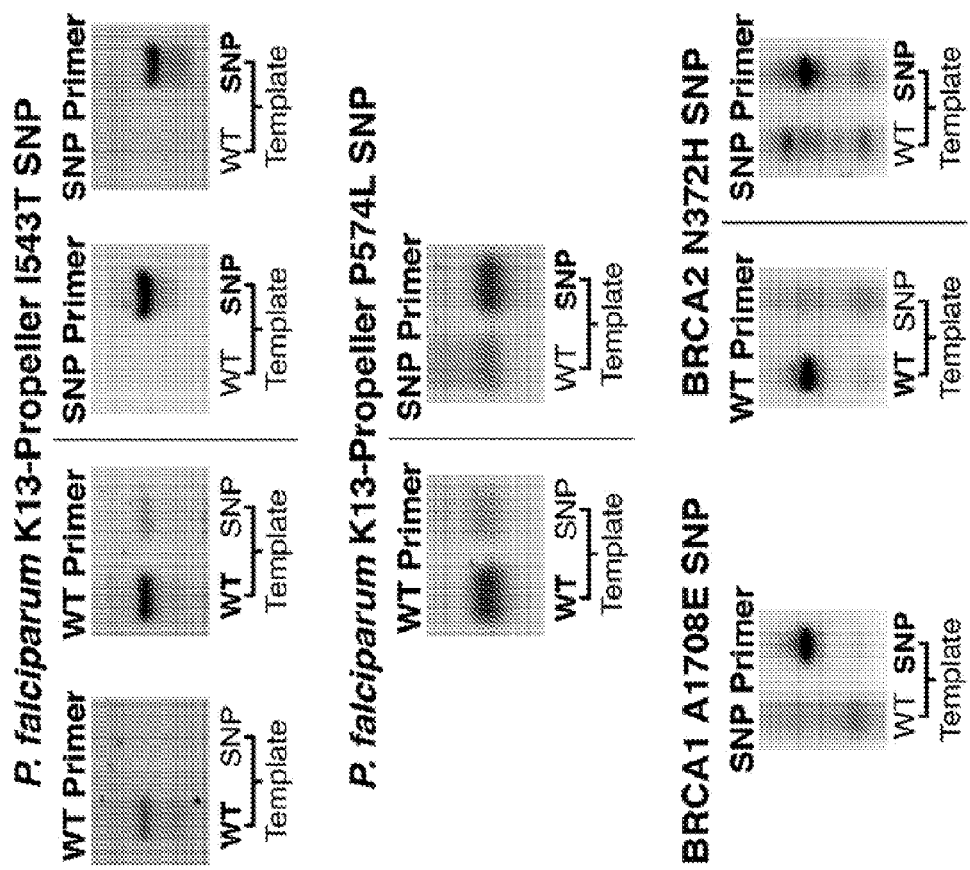
FIG. 6 displays images of agarose gels after electrophoresis of the products of recombinase polymerase amplification (RPA) reactions using the SNP-specific remote toehold primers as the forward primer and using a conventional reverse primer. WT primers and SNP primers show substantially higher amounts of amplified product for their intended WT and SNP templates, respectively.

FIG. 6 shows agarose gels from experiments using remote toehold primers to amplify four sets of template sequences. Two pairs of sequences were taken from the *Plasmodium falciparum* genome where the I543T and P574L SNPs in the K13-propeller region have been associated with resistance to artemisinin, a first-line drug against *P. falciparum* malaria. For the I543T mutation, two remote toehold primers designed to selectively amplify the wild-type sequence demonstrated successful amplification of the wild-type template but little to no amplification of the mutant template. This result is evidenced in the agarose gels where the product is clearly much more visible for the wild-type template compared to the mutated SNP template (FIG. 6). Similarly, two remote toehold primers for the I543T SNP, selectively amplified the mutated template compared to the wild-type one. Remote toehold primers also specifically amplified K13-propeller P574L SNP and wild-type templates as indicated in the agarose gels.

Additional experiments on BRCA1 and BRCA2 mutations from the human genome confirmed the specificity of the remote toehold primers (FIG. 6). A SNP primer successfully amplified the BRCA1 A1708E SNP without amplifying the wild-type template. Wild-type and SNP primers for the BRCA2 N372H mutation also selectively amplified their corresponding templates.

SNP-Specific Intramolecular Competitive Primers

Intramolecular competitive (IC) primers provide enhanced SNP specificity by integrating a wild-type and SNP targeting hairpins into the same primer. The design of the IC primers is illustrated in FIG. 7 and employs two hairpins each paired with a short 3' toehold and separated from one another by a 5 to 15 nt spacer domain. The hairpin at the 3' end of the primer is designed to bind to the template sequence to be amplified (the mutant in FIG. 7), while the hairpin at the 5' end of the primer is designed to bind to a template sequence that should not be amplified (the wild-type in FIG. 7). Both hairpins have short forward and reverse toeholds of between 4 to 10 nts; thus, both should exhibit single-nucleotide specificity based on the same arguments made for the SNP-specific hairpin primers above. Positioning both hairpins within the same primer enables both hairpins to effectively compete for binding to the template, leading to improved specificity, which compensates for the decreased binding affinity of the IC primers compared to those with extended docking sites. As illustrated in FIG. 7, in the presence of the off-target wild-type template, the binding of the 5' hairpin does not result in amplification since the 3' end of the primer is not bound to the template. In contrast, the presence of the on-target mutant template enables the 3' hairpin to bind and complete the branch migration to unwind the stem. The bound toehold domain then provides a 3' end for the DNA polymerase to extend.

Figure 8:
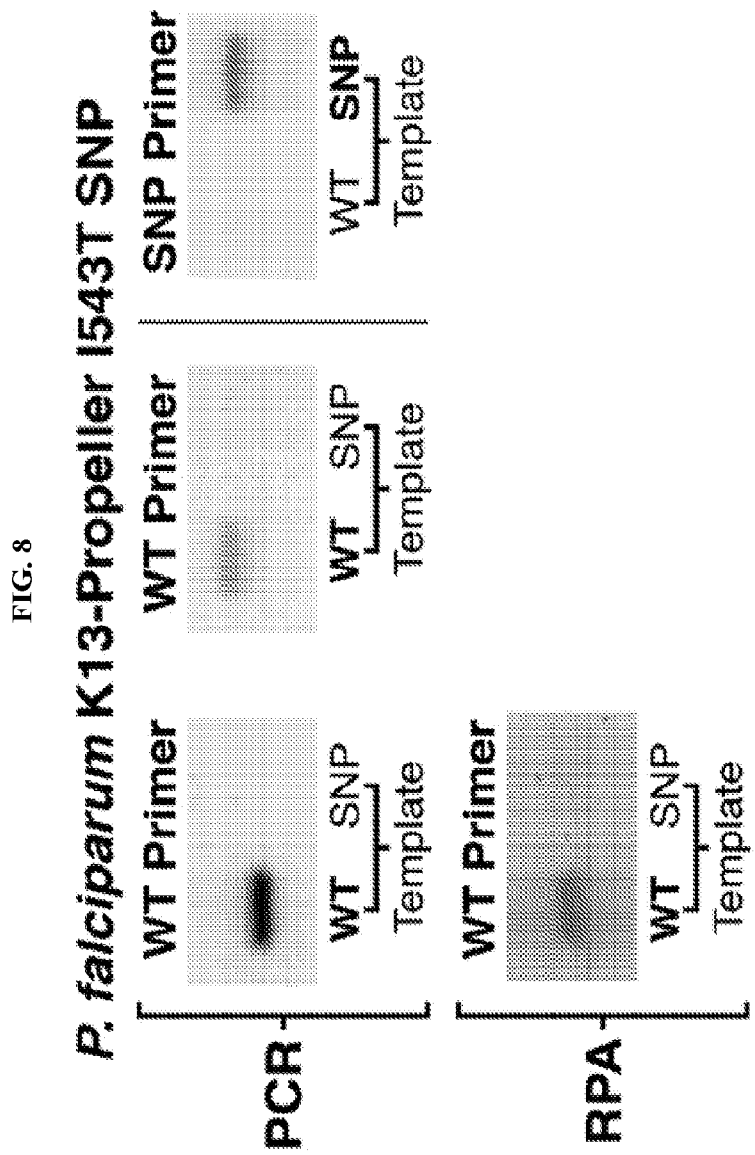
FIG. 8 displays images of agarose gels after electrophoresis of the products of PCR and recombinase polymerase amplification (RPA) reactions using the SNP-specific intramolecular competitive forward primers and conventional reverse primers. WT primers selectively amplify the wild-type DNA templates in both PCR and isothermal RPA reactions. SNP primers selectively amplify the mutant SNP templates in PCR reactions.

FIG. 8 shows agarose gels visualizing the products of PCR and RPA reactions using the intramolecular competitive (IC) primers. All primers were designed to amplify either the wild-type or mutated I543T SNP from the K13-propeller region of *P. falciparum*. In PCR reactions using a 50° C. primer hybridization temperature, FIG. 8 shows successful amplification of the wild-type sequence by two IC primers and amplification of the I543T SNP template by one IC primer. In all three cases, the unwanted template leads to undetectable levels of amplification in the agarose gel. Based on these successful results from PCR, we were able to confirm successful amplification of the wild-type K13-propeller sequence in isothermal RPA reactions as evidenced by the gel image at the bottom of FIG. 8.

Amplification Primer and Displacer Pairs with Single-Nucleotide Specificity

A weakness of the SNP-specific primers described above is that they all contain the sequence of the SNP selected to be amplified. Thus, the amplicons they produce must necessarily contain the sequence of the SNP, even if a spurious hybridization event causes the primer to amplify an off-target, non-mutated template DNA. Off-target templates amplified in this way are indistinguishable from on-target amplicons and can lead to false positive results in diagnostics if the primers are not carefully designed and tested. Consequently, alternative primer designs that amplify SNPs without containing the SNP sequence itself would be attractive for highly specific amplification in low-cost liquid biopsies.

We have developed a system that can accomplish this task in isothermal amplification reactions using a primer and a so-called displacer strand. The two strands do not require any modified bases and are thus ideal for implementing in a low-cost liquid biopsy format. The general design of primer/displacer pairs is illustrated in FIG. 9. Both strands feature a docking site, a spacer domain 5 to 15 nts or more in length, a short toehold 3 to 10 nts in length, and a branch migration domain 8 to 20 nts or more in length; however, these domains occur in the opposite order in the two strands. In addition, the displacer strand features a 3' domain 4 to 15 nts in length designed to not hybridize with the template, which prevents polymerization of the displacer. The docking site, toehold, and branch migration domain of the primer are perfectly complementary to both the on-target and off-target templates (mutant and wild-type templates, respectively, in FIG. 9). For the displacer strand, the docking site and branch migration domain are perfectly complementary to both templates; however, the toehold domain is only complementary to the off-target template and establishes the SNP-specificity of the primer/displacer system.

In the amplification reaction, both strands can initially bind to the template via their docking sites, which have high melting temperatures. Once docked, the primer and displacer strand branch migration domains compete for binding to template. Since the branch migration domains are identical for both strands and they are perfectly complementary to either template, the strand that ultimately completes the branch migration is determined by the affinity of its toehold domain for the template. For the off-target template, the reverse toehold of the displacer domain is engineered to have slightly higher affinity than the forward toehold of the primer strand. Consequently, the displacer branch migration domain binds to the template, displacing the primer and preventing it from polymerizing. For the on-target template, the mismatch between the mutant template and the reverse toehold of the displacer strand reduces its affinity for the template. This change in hybridization free energy enables the primer branch migration domain to bind to the mutant template and form a substrate suitable for extension by the DNA polymerase. Since the primer binds only up to the branch migration domain, polymerization leads to an amplicon where the base at the SNP site is defined by the sequence of the template, not that of the primer itself. As a result, potential spurious extension of the primer on the off-target DNA template does not directly lead to a mutant amplicon being generated.

Spurious extension of the primer on off-target templates, however, does cause the spacer of the primer to be incorporated into the resulting amplified DNA. This extra domain can have a negative effect on subsequent amplification cycles since it leads to preferential hybridization of by the primer. A modified primer/displacer design that avoids this phenomenon is shown in FIG. 10. In this design, the primer and displacer strands lack docking sites and spacer domains. As a result, their sequences are both entirely complementary to the off-target template (wild-type template in FIG. 10). To compensate for removal of the docking sites, the forward and reverse toeholds can be extended to facilitate their binding to the template. Just as with the original design, careful tuning of toehold length and sequence can be used to ensure that the branch migration proceeds for the displacer strand in the presence of the off-target RNA, thereby inhibiting polymerization. Conversely, the mismatch in the reverse toehold in the presence of the on-target mutant template tilts the reaction to the primer, enabling it to hybridize with the template and undergo extension by the DNA polymerase. Importantly, no additional sequences are added to the amplicon by the primer, which prevents spurious amplicons from being enriched in subsequent cycles.

Figure 11:
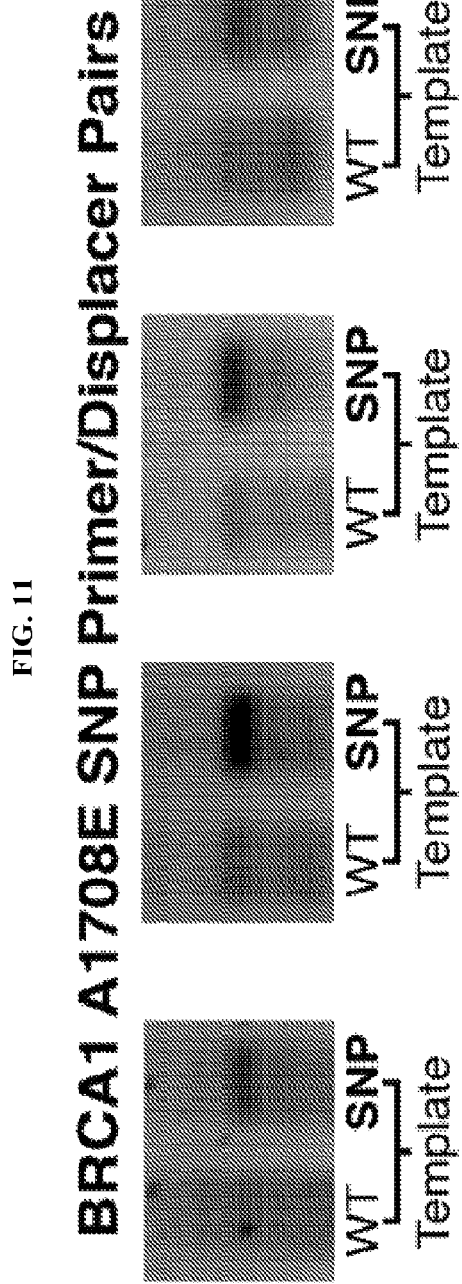
FIG. 11 displays images of agarose gels after electrophoresis of the products of RPA reactions using the primer/displacer pairs with docking sites. All four primer pairs show substantially higher amplification of the desired SNP template compared to the wild-type template for the BRCA1 A1708E SNP associated with breast cancer.

Results from experimental testing of four primer/displacer pairs designed to specifically amplify the BRCA1 A1708E SNP are shown in FIG. 11. Both the primers and displacers in these experiments employed docking domains and were evaluated in isothermal RPA reactions. Agarose gels of the RPA products showed substantial increases in the amplification of the SNP template compared to the wild-type (WT) template as expected.

Competitive Riboregulator Compositions for Enrichment of Minority Species

Figure 12:
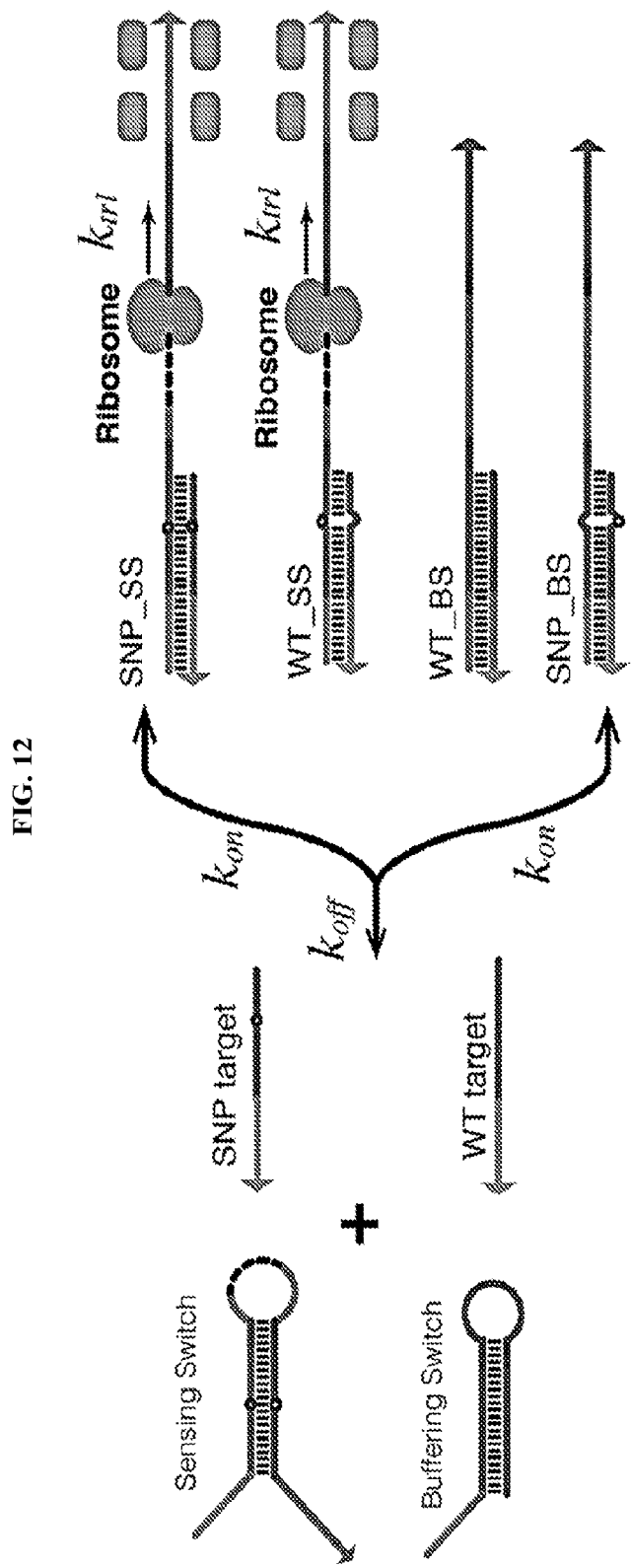
FIG. 12 describes competitive riboregulator systems comprising sets of two or more SNP-specific riboregulators that are designed to recognize slightly different target sequences. In such systems, a riboregulator for detecting a SNP of interest produces a reporter protein upon binding the mutant nucleic acid of interest. At the same time, one or more buffering switches can preferentially bind to wild-type targets to reduce their background effect on the reaction.

Since ctDNA is the minority species in the total DNA circulating in the blood, even after amplification procedures it will often be outnumbered by wild-type DNA species by one or more orders of magnitude. It can thus be difficult for a SNP-specific riboregulator to detect the mutated nucleic acid when it is much more likely to interact with off-target wild-type nucleic acids. Competitive riboregulator compositions enable these minority nucleic acid species to be detected even in a high background of wild-type nucleic acids by using buffering strands that remove wild-type species from the reaction. The general design of these systems is shown in FIG. 12. They consist of two riboregulators or hairpin RNA molecules: one is a SNP-specific riboregulator without a docking site, termed the sensing switch; the other is a SNP-specific riboregulator or hairpin without a docking site, termed the buffering switch. The sensing switch is designed to detect the mutated target and contains the coding sequence for the main reporter protein in a diagnostic. The reporter protein can be lacZ, GFP, luciferase, or some other widely used protein/enzymatic reporter. The buffering switch is designed to bind to the wild-type nucleic acid and its composition can vary depending on the desired implementation. The buffering switch can simply be a short hairpin lacking an RBS in its loop, as illustrated in FIG. 12, or it can be a functional riboregulator that outputs a different reporter that can be used to determine the levels of wild-type target.

When both the sensing switch and the buffering switch are exposed to a mixture of SNP and wild-type nucleic acids, they will compete for binding to both species. Since the buffering switch has higher affinity for the wild-type species, it will outcompete the sensing switch for binding to these targets. Similarly, the sensing switch will outcompete the buffer switch for binding to the mutant SNP target and begin translating the reporter. Unwanted binding will occur between the sensing switch and the wild-type target and between the buffering switch and the mutant target. However, as depicted in FIG. 12, these off-target interactions will have different reaction rate constants than the on-target ones. In particular, the rate constant for the forward reaction $k_{on}$ (target/trigger hybridization) will be less than that of the reverse reaction $k_{off}$ (target/trigger dissociation), which means that any target/switch complex formed by the off-target interaction will soon dissociate and leave the target species free to bind to the intended switch strands. This dissociation reaction is aided by the short toehold domain and the absence of docking sites for the sensing and buffering strands. As the interaction between the two switches and the ensemble of target nucleic acids continues, the reversible off-target binding coupled with favorable on-target binding interactions will eventually lead to activation of the sensing switch by the mutant targets. At the same time, the majority wild-type species interfering with detection have been removed from the ensemble through favorable binding to the buffering switch. It should be noted that more than two competing hairpins or riboregulators can be used to preferentially enrich minority species. In these systems, additional buffering switches can be deployed to remove alternative target SNPs or very homologous wild-type species from the reaction to facilitate detection of a cancer- or disease-associated SNP by the sensing riboregulator.

Experimental Protocols

DNA Template Preparation: All DNA oligonucleotides were purchased from Integrated DNA Technologies. To ensure all templates were correctly synthesized, wild-type and SNP templates were inserted into pET15b-derived vectors. Constructs were cloned inside DH5α (endA1 recA1 gyrA96 thi-1 glnV44 relA1 hsdR17($r_K^-$ $m_K^+$) λ-) and sequenced.

Polymerase Chain Reaction Protocol: Phusion® High-Fidelity PCR Master Mix with HF Buffer (New England Biolabs) was used for the PCR amplification of the templates. Each 10 μL PCR reaction contained 0.5 μM of the forward IC primer, 0.5 μM of a standard reverse primer, and 11 pg of template. A 50° C. melting temperature was used in the thermal cycler PCR program. PCR products were then run on a 2.5% agarose gel.

RPA Protocol with Remote Toehold Primers: The RPA reactions were performed according to manufacturer's protocol (TwistAmp® Basic, TwistDx). Briefly, for a 50 μL RPA reaction, 0.48 μM of the forward remote toehold primers, 0.48 μM of a standard reverse primer, 7.2×10⁷ copies of the template, 29.5 μL of rehydration buffer were added into each freeze-dried enzyme tube. Next, 2.5 μL of 280 mM magnesium acetate was added to the reaction mixture. Reactions were incubated at 37° C. for 30 minutes. Finally, 1 μL of the reaction product was run on a 2% agarose gel.

RPA Protocol with Primer/Displacer Pairs: The RPA protocol for the primer displacer pairs was the same as that used for the remote toehold primers with a few differences. 0.48 μM of the blocker strand was used in the reaction, along with 0.48 μM each of the corresponding forward primer and a conventional reverse primer. An amount between 5 pM and 50 pM of the template was used in each reaction. Reactions were incubated at 37° C. for 40 minutes prior to characterization on 2% agarose gels.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method for preferential amplification of a target DNA molecule comprising a single nucleotide polymorphism (SNP) mutation, wherein the method comprises:
    (a) contacting a SNP-specific remote toehold primer to a sample comprising a target DNA molecule, wherein the SNP-specific remote toehold primer comprises (i) a 5' docking site complementary to the target DNA molecule, (ii) a spacer domain not complementary to the target DNA molecule, and (iii) a 3' mutant targeting remote toehold domain which is three to four nucleotides in length and complementary to a region in the target DNA molecule comprising the SNP mutation, and whereby the SNP-specific remote toehold primer associates with the target DNA molecule;
    (b) extending from the 3' end of the mutant targeting remote toehold domain of the SNP-specific remote toehold primer along the target DNA molecule with a DNA polymerase and deoxynucleotides using the target DNA molecule as a template,
    wherein, in the presence of the target DNA molecule comprising the SNP mutation, the mutant targeting remote toehold domain binds to the region in the target DNA molecule comprising the SNP mutation, thereby positioning the 3' end of the mutant targeting remote toehold domain to prime polymerization along the target DNA molecule as a template by the DNA polymerase, and wherein, in the presence of the target DNA molecule not containing the SNP mutation, the mutant targeting remote toehold domain does not bind to the DNA template and extending from the 3' end of the mutant targeting remote toehold domain by the DNA polymerase using the target DNA molecule as a template does not occur; and (c) detecting a product, which comprises the extended mutant targeting remote toehold domain of step (b), indicating the presence of said target DNA molecule comprising the SNP mutation in the sample.

2. The method of claim 1, further comprising repeating steps (a) and (b) along with a conventional amplification primer in the reverse direction to allow amplification of the product.

3. The method of claim 1, wherein the mutant targeting remote toehold domain is 4 nucleotides in length.

4. The method of claim 1, wherein detecting the product indicating the presence of said target DNA molecule comprising the SNP mutation in the sample is a positive or negative indicator of a disease-associated mutation in said sample.

* * * * *